(12) United States Patent
Blackford

(10) Patent No.: US 9,925,027 B1
(45) Date of Patent: Mar. 27, 2018

(54) INCONTINENCY ABATEMENT SYSTEM

(76) Inventor: Richard Blackford, Venice, FL (US)

(*) Notice: Subject to any disclaimer, the term of this patent is extended or adjusted under 35 U.S.C. 154(b) by 43 days.

(21) Appl. No.: 13/343,793

(22) Filed: Jan. 5, 2012

Related U.S. Application Data

(63) Continuation-in-part of application No. 12/398,787, filed on Mar. 5, 2009, now Pat. No. 7,821,446.

(51) Int. Cl.
| | |
|---|---|
| A61F 2/00 | (2006.01) |
| A61F 5/00 | (2006.01) |
| A63B 23/20 | (2006.01) |
| A63B 21/005 | (2006.01) |

(52) U.S. Cl.
CPC .......... *A61F 2/0009* (2013.01); *A61F 5/0093* (2013.01); *A61F 2250/001* (2013.01); *A63B 21/005* (2013.01); *A63B 23/20* (2013.01)

(58) Field of Classification Search
CPC .............. A61F 2250/001; A61F 2/0009; A61F 5/0093; A61F 21/005; A61B 21/023; A61B 23/20

USPC ........ 600/29–31, 32, 38; 128/845, 883, 885, 128/887; 604/327, 337; 601/46, 23
See application file for complete search history.

(56) References Cited

U.S. PATENT DOCUMENTS

| | | | | |
|---|---|---|---|---|
| 5,865,715 | A * | 2/1999 | Wallick ..................... | 482/124 |
| 6,258,015 | B1 * | 7/2001 | Blackford et al. ............ | 482/124 |
| 6,896,650 | B2 * | 5/2005 | Tracey et al. ................. | 600/29 |
| 2002/0147382 | A1 * | 10/2002 | Neisz et al. .................... | 600/29 |
| 2009/0292262 | A1 * | 11/2009 | Adams et al. ................ | 604/264 |

* cited by examiner

*Primary Examiner* — Christine H Matthews
*Assistant Examiner* — Joshua D Lannu

(57) ABSTRACT

A body having first and second segments is shaped to include distal and proximal and intermediate portions. The segments are hollow to form a chamber. A hinge pin in the proximal portion rotatably couples the segments. A spring within the chamber urges the segments to an open orientation. A locking assembly within the chamber selectively holds the segments in the open orientation and selectively holds the segments in the closed orientation.

4 Claims, 3 Drawing Sheets

FIG. 6
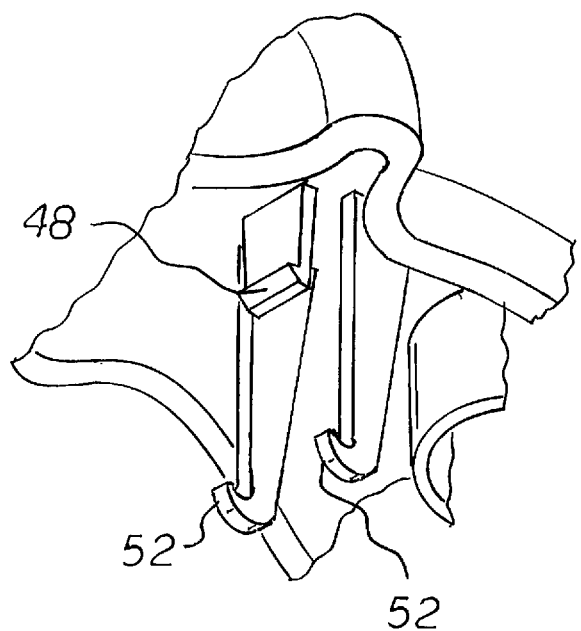
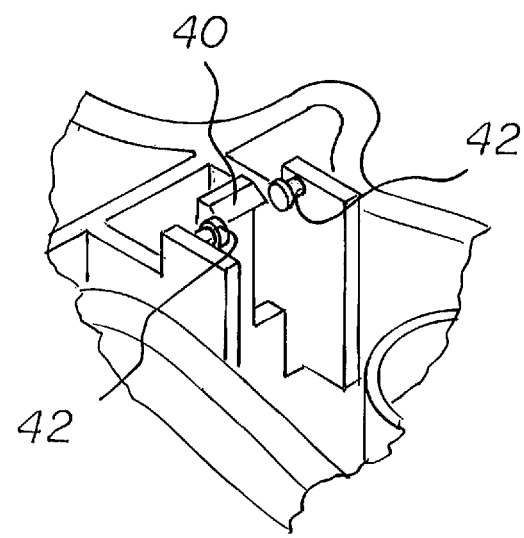
FIG. 7

INCONTINENCY ABATEMENT SYSTEM

RELATED APPLICATION

The present application is a continuation-in-part of U.S. patent application Ser. No. 12/387,676 filed May 6, 2009, now U.S. Pat. No. 8,118,726, the subject matter of which is incorporated herein by reference.

BACKGROUND OF THE INVENTION

Field of the Invention

The present invention relates to an incontinency abatement system and more particularly pertains to eliminating unintended fecal discharge in a safe, convenient and economical manner.

Description of the Prior Art

The use of incontinency abatement systems of known designs and configurations is known in the prior art. More specifically, incontinency abatement systems of known designs and configurations previously devised and utilized for the purpose of eliminating unintended fecal discharge are known to consist basically of familiar, expected, and obvious structural configurations, notwithstanding the myriad of designs encompassed by the crowded prior art which has been developed for the fulfillment of countless objectives and requirements.

While the prior art devices fulfill their respective, particular objectives and requirements, they do not describe an incontinency abatement system that allows for eliminating unintended fecal discharge in a safe, convenient and economical manner.

In this respect, the incontinency abatement system according to the present invention substantially departs from the conventional concepts and designs of the prior art, and in doing so provides an apparatus primarily developed for the purpose of eliminating unintended fecal discharge in a safe, convenient and economical manner.

Therefore, it can be appreciated that there exists a continuing need for a new and improved incontinency abatement system which can be used for eliminating unintended fecal discharge in a safe, convenient and economical manner. In this regard, the present invention substantially fulfills this need.

SUMMARY OF THE INVENTION

In view of the foregoing disadvantages inherent in the known types of incontinency abatement systems of known designs and configurations now present in the prior art, the present invention provides an improved incontinency abatement system. As such, the general purpose of the present invention, which will be described subsequently in greater detail, is to provide a new and improved incontinency abatement system and method which has all the advantages of the prior art and none of the disadvantages.

To attain this, the present invention essentially comprises an incontinency abatement system. First provided is a body having first and second segments shaped to include distal and proximal and intermediate portions. The segments are hollow to form a chamber. A hinge pin in the proximal portion rotatably couples the segments. A spring within the chamber urges the segments to an open orientation. A locking assembly within the chamber selectively holds the segments in the open orientation and selectively holds the segments in the closed orientation.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved incontinency abatement system which has all of the advantages of the prior art incontinency abatement systems of known designs and configurations and none of the disadvantages.

It is another object of the present invention to provide a new and improved incontinency abatement system which may be easily and efficiently manufactured and marketed.

It is further object of the present invention to provide a new and improved incontinency abatement system which is of durable and reliable constructions.

An even further object of the present invention is to provide a new and improved incontinency abatement system which is susceptible of a low cost of manufacture with regard to both materials and labor, and which accordingly is then susceptible of low prices of sale to the consuming public, thereby making such incontinency abatement system economically available to the buying public.

Even still another object of the present invention is to provide an incontinency abatement system for eliminating unintended fecal discharge in a safe, convenient and economical manner.

Lastly, it is an object of the present invention to provide a new and improved incontinency abatement system for eliminating unintended fecal discharge, such eliminating being done in a safe, convenient and economical manner.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated the primary and preferred embodiment of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is an upwardly looking perspective illustration of the long and short fingers and hooks.

FIG. 7 is a downwardly looking perspective illustration of the fixed finger and hook and rollers.

The same reference numerals refer to the same parts throughout the various Figures illustrating the primary embodiment of the invention.

DESCRIPTION OF THE PREFERRED EMBODIMENT

Figures 1, 2, 3:
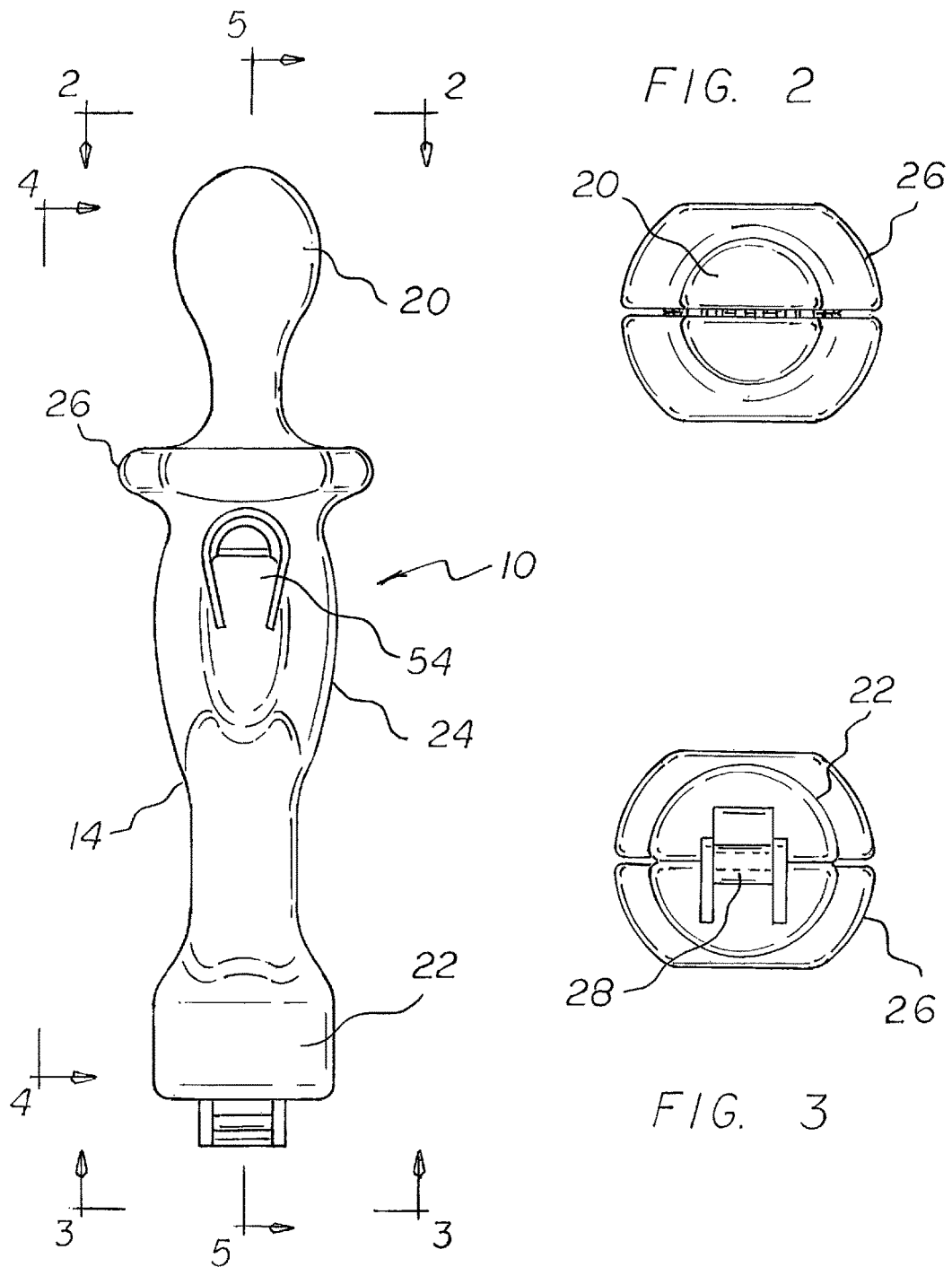
FIG. 1 is a front elevational view of an incontinency abatement system constructed in accordance with the principles of the present invention.
FIG. 2 is a plan view of the system taken along line 2-2 FIG. 1.
FIG. 3 is a bottom view of the system taken along line 3-3 FIG. 1.
Figure 4:
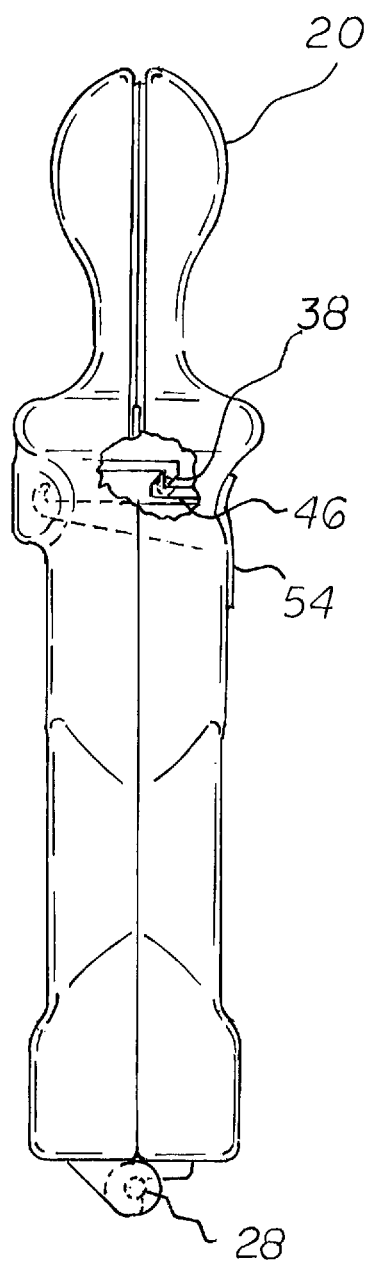
FIG. 4 is a side elevational view of the system taken along line 4-4 FIG. 1.
Figure 5:
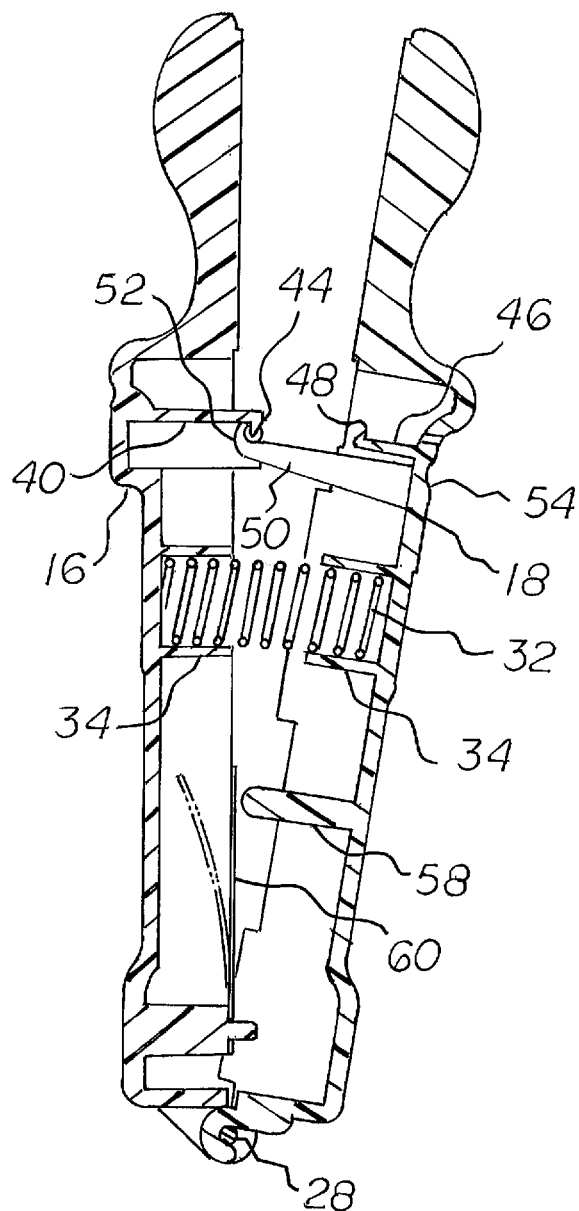
FIG. 5 is a cross sectional view taken along line 5-5 of FIG. 1 but with the body in the open orientation.

With reference now to the drawings, and in particular to FIG. 1 thereof, the preferred embodiment of the new and improved incontinency abatement system embodying the principles and concepts of the present invention and generally designated by the reference numeral 10 will be described.

The present invention, the incontinency abatement system 10 is comprised of a plurality of components. Such components in their broadest context include a body, a spring and a locking assembly. Such components are individually configured and correlated with respect to each other so as to attain the desired objective. The incontinency abatement system 10 is for eliminating unintended fecal discharge in a safe, convenient and economical manner.

First provided is a body 14. The body has a first segment 16 and a similarly configured second segment 18. The segments are shaped to include an enlarged generally spherical distal portion 20, an enlarged generally cylindrical proximal portion 22, and an enlarged intermediate portion 24. An annular stopper 26 is provided between the distal and intermediate portions. The stopper has a circumference greater than the circumference of the distal and proximal and intermediate portions. The first and second segments are hollow to form a chamber. A hinge pin 28 is provided in the proximal portion of the body rotatably coupling the first and second segments. The first and second segments are rotatable to a closed orientation with the first and second segments in contact with each other.

The first and second segments are rotatable to an open orientation with the first and second segments spaced to form a V-shaped slit intermediate the first and second segments.

Next provided is a coil spring 32 having opposed ends within the chamber between and in contact with the first and second segments. The coil spring urges the segments to the open orientation. Next provided are cylindrical keepers 34 within the chamber formed in the intermediate sections of the first and second segments for receiving and positioning the ends of the coil spring.

A locking assembly 38 is provided within the chamber between the coil spring and the stopper. The locking assembly includes a fixed finger 40 extending from the first segment. The fixed finger has a free end formed with a downwardly extending fixed hook 42 and rollers 44. The locking assembly also includes a pivotable short finger 46 extending from the second segment. The short finger has a free end formed with an upwardly extending short hook 48 adapted to couple with the fixed hook to hold the first and second segments in the closed orientation. The locking assembly also includes a pivotable long finger 50 extending from the second segment parallel with the short finger. The long finger has a free end formed with an upwardly extending long hook 52 adapted to couple with the rollers to hold the first and second segments in the open orientation. A pivotable flap 54 is formed in the second segment pivotably supporting the short and long fingers. The flap has a normal position with the long and short fingers pivoted upwardly into contact with the fixed finger for selectively holding the first and second segments in a desired orientation. The flap has a depressed position with the long and short fingers pivoted downwardly away from the fixed finger for selective movement of the first and second segments between orientations.

Lastly provided is a positioning finger 58 in the chamber between the coil spring and the hinge pin. The positioning finger extends from the second segment with a free end located in the first segment when in the closed orientation. Next provided is a leaf spring 60 having a lower end coupled to the first segment adjacent to the pivot pin. The leaf spring has an upper end adapted to be contacted by the finger when in the closed orientation tending to cause a clicking sound when moving between orientations.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An incontinency abatement system comprising:
   a body having first and second segments, each comprising distal and proximal and intermediate portions, the segments having similarly shaped exterior surfaces, the segments being hollow to form a chamber, a hinge pin in the proximal portion of the first or second segment rotatably coupling the segments for pivoting the proximal and intermediate portions towards and away from each other;
   a spring within the chamber urging the segments to an open orientation; and
   a locking assembly within the chamber to selectively hold the segments in the open orientation with the distal and proximal and intermediate portions spaced from each other and to selectively hold the segments in a closed orientation with the distal and proximal and intermediate portions in contact with each other;

wherein the locking assembly includes a fixed finger extending from the first segment, the fixed finger having a free end formed with a downwardly extending fixed hook and rollers, the locking assembly also including a pivotable short finger extending from the second segment, the short finger having a free end formed with an upwardly extending short hook adapted to couple with the fixed hook to hold the first and second segments in the closed orientation, the locking assembly also including a pivotable long finger extending from the second segment parallel with the short finger, the long finger having a free end formed with an upwardly extending long hook adapted to couple with the rollers to hold the first and second segments in the open orientation.

2. The system as set forth in claim 1 and further including:
a pivotable flap formed in the second segment pivotably supporting the short and long fingers, the flap having a normal position with the long and short fingers pivoted upwardly into contact with the fixed finger for selectively holding the first and second segments in a desired orientation, the flap having a depressed position with the long and short fingers pivoted downwardly away from the fixed finger for selective movement of the first and second segments.

3. The system as set forth in claim 1 and further including:
a positioning finger in the chamber extending from the second segment with a free end located in the first segment when in the closed orientation, a leaf spring having a lower end coupled to the first segment adjacent to the hinge pin, the leaf spring having an upper end adapted to be contacted by the positioning finger when in the closed orientation tending to urge the positioning finger and second segment to the open orientation.

4. An incontinency abatement system comprising, in combination:
a body having a first segment and a similarly configured second segment, the segments being shaped to include an enlarged generally spherical distal portion and an enlarged generally cylindrical proximal portion and an enlarged intermediate portion, an annular stopper between the distal and intermediate portions, the stopper having a circumference greater than a circumference of the distal and proximal and intermediate portions, the first and second segments being hollow to form a chamber, a hinge pin in the proximal portion of the body rotatably coupling the first and second segments, the first and second segments rotatable to a closed orientation with the first and second segments in contact with each other, the first and second segments rotatable to an open orientation with the first and second segments, including the distal portions and the proximal portions and the intermediate portions, spaced to form a V-shaped slit intermediate the first and second segments;

a coil spring having opposed ends within the chamber between and in contact with the first and second segments, the coil spring urging the segments to the open orientation, cylindrical keepers within the chamber formed in the intermediate portions of the first and second segments for receiving and positioning the ends of the coil spring;

a locking assembly within the chamber between the coil spring and the stopper, the locking assembly including a fixed finger and rollers extending from the first segment, the fixed finger having a free end formed with a downwardly extending fixed hook and rollers, the locking assembly also including a pivotable short finger extending from the second segment, the short finger having a free end formed with an upwardly extending short hook adapted to couple with the fixed hook to hold the first and second segments in the closed orientation, the locking assembly also including a pivotable long finger extending from the second segment parallel with the short finger, the long finger having a free end formed with an upwardly extending long hook adapted to couple with the rollers to hold the first and second segments in the open orientation, a pivotable flap formed in the second segment pivotably supporting the short and long fingers, the flap having a normal position with the long and short fingers pivoted upwardly into contact with the fixed finger for selectively holding the first and second segments in a desired orientation, the flap having a depressed position with the long and short fingers pivoted downwardly away from the fixed finger for selective movement of the first and second segments between orientations; and a positioning finger in the chamber between the coil spring and the hinge pin, the positioning finger extending from the second segment with a free end located in the first segment when in the closed orientation, a leaf spring having a lower end coupled to the first segment adjacent to the hinge pin, the leaf spring having an upper end adapted to be contacted by the positioning finger when in the closed orientation tending to cause a clicking sound when changing orientations.

* * * * *